Figure 1:
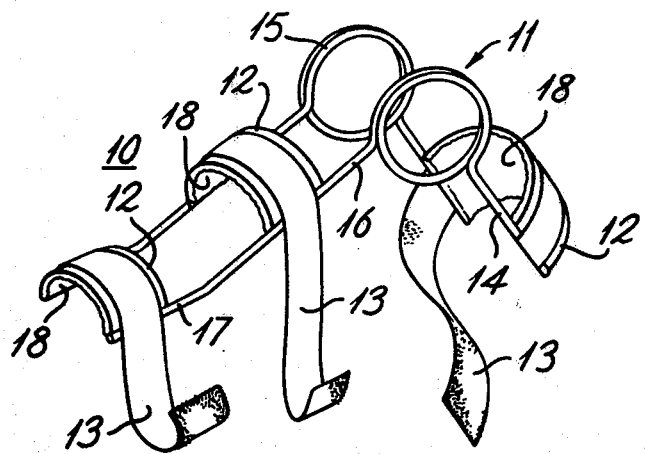

United States Patent [19]
Evans et al.

[11] 4,441,489
[45] Apr. 10, 1984

[54] ORTHOPAEDIC SPLINTS

[75] Inventors: David M. Evans, Farnham Common; Barry O. Weightman, Thames Ditton, both of England

[73] Assignee: National Research Development Corporation, London, England

[21] Appl. No.: 355,623

[22] Filed: Mar. 8, 1982

[30] Foreign Application Priority Data

Mar. 10, 1981 [GB] United Kingdom ............... 8107537

[51] Int. Cl.³ .............................................. A61F 5/10
[52] U.S. Cl. ..................................... 128/77; 128/87 A
[58] Field of Search .................. 128/77, 87 A, 87 R; 272/67, 68, 140

[56] References Cited

U.S. PATENT DOCUMENTS 4,220,334 9/1980 Kanamoto et al. ............... 128/77 X
4,243,026 1/1981 Barber ............................. 128/87 A

FOREIGN PATENT DOCUMENTS 1529910 6/1968 France ................................ 128/77
929317 6/1963 United Kingdom .

OTHER PUBLICATIONS

Barron & Saad, "Management of Extensor Tendon Injuries" from The Hand: Operative Plastic and Reconstruction Surgery, published 1980.

Primary Examiner—John D. Yasko
Attorney, Agent, or Firm—Cushman, Darby & Cushman

[57] ABSTRACT

An orthopaedic splint is provided for treatment of injury to the extensor tendon distal to the DIP joint in the finger, the splint serving to hold the DIP joint in hyperextension and the PIP joint in flexion, while allowing restrained extension of the PIP joint. The splint suitably involves first and second portions each including at least one plate curved to seat transversely over or under a finger, the first portion also being longitudinally inclined and provided with strapping to hold the DIP joint in hyperextension, and the portions being resiliently and hingedly interconnected to hold the PIP joint as required. This interconnection conveniently involves like springs on respectively opposite sides of the PIP joint, the springs preferably being of mutually parallel flat spiral form.

9 Claims, 4 Drawing Figures

ORTHOPAEDIC SPLINTS

This invention concerns orthopaedic splints and more particularly such splints for use in connection with the distal interphalangeal joint, hereinafter referred to as the DIP joint.

The invention has in fact been developed primarily for use in treatment of the so-called mallet deformity. This deformity is discussed in the book "The Hand: Operative Plastic and Reconstructive Surgery", edited by Barron and Saad, and published by Churchill Livingston, 1980. This book indicates that a mallet deformity is the result of injury, open or closed, to the extensor tendon distal to the proximal interphalangeal joint, hereinafter referred to as the PIP joint. Conventional treatment for mallet deformity is said to comprise splinting of the DIP joint in slight hyperextension. This splinting is appropriate in the case of a closed deformity, possibly after an initial period involving a cast extending to the forearm, or following surgery in the case of an open deformity.

Difficulty can arise with the splinting just described because the PIP joint is left free to move. The ruptured tendon ends are maintained in close proximity only if there is restricted extension of the PIP joint which otherwise tenses the lateral bands with flexion and separates the divided terminal extensor. However lack of movement at the PIP joint during the relevant period of about six weeks is itself problematical in tending to produce tendon contracture.

An object of the present invention is to improve this situation and this is effected by the provision of a splint which holds the DIP joint in slight hyperextension and the PIP in flexion, while allowing restrained extension of the PIP joint.

The benefit of this different situation is that the additional splinting of the PIP joint in flexion relaxes the extensor tendon distally so that small movements of this joint can be made without separation of the tendon ends, and these movements allow exercise.

The proposed splint suitably comprises a first portion and a second portion respectively for location proximally and distally of the PIP joint, said first portion holding the DIP joint in hyperextension, and said first and second portions being resiliently and hingedly interconnected to hold the PIP joint in flexion while allowing restrained extension against the spring force of such interconnection.

Normally each of said first and second portions will include at least one plate curved to seat in palmar or dorsal disposition over a phalanx, with at least said first portion having strapping to hold the same so seated.

Conveniently a common spring structure is provided to afford both the resilience and hingeing capability of the interconnection between the first and second portions. Also, such structure conveniently comprises like spring formations locatable in respectively opposed dispositions laterally of the PIP joint, suitable springs being of flat spirally wound formations in mutually parallel dispositions.

Figure 2:
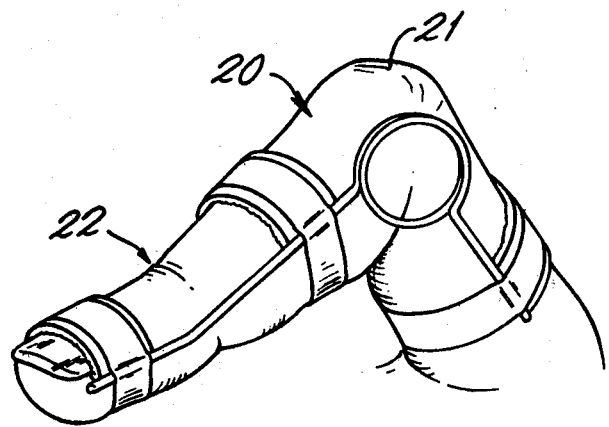
Figure 3:
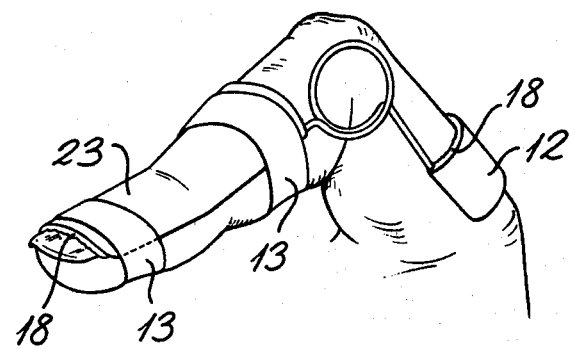
Figure 4:
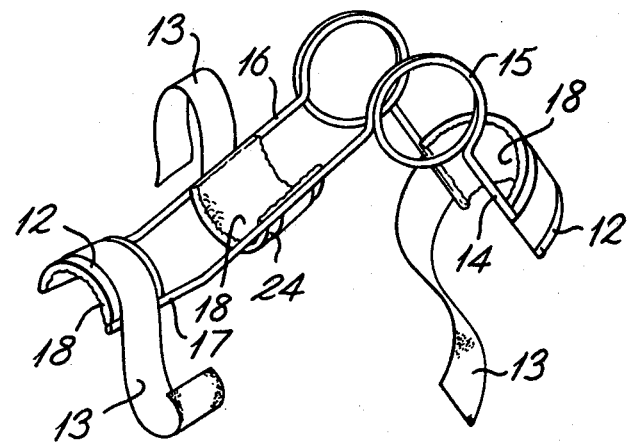

A fuller understanding of the invention will be gained from the following description of three forms thereof, given by way of example, with reference to the accompanying drawings, in which:

FIG. 1 schematically illustrates in perspective view one form of splint according to the invention, FIG. 2 similarly illustrates the splint of FIG. 1 applied to a finger, FIG. 3 illustrates in application to a finger another form of splint according to the invention by modification of the splint of FIG. 1, and FIG. 4 illustrates yet another such modified form of splint.

The splint of FIG. 1 is denoted generally at 10 and comprises two like elongate members 11 formed to a particular shape as described below, three similar curved plates 12 interconnecting the members 11, and three straps 13 respectively connected with the plates 12.

The shape of each member 11 involves a first end portion 14 which continues at one end into a flattened spiral portion 15, and then into a remainder consisting of a further intermediate portion 16 and a second end portion 17. These portions are all generally coplanar, the portions 16 and 17 extend generally perpendicularly to portion 14, and the portion 17 is inclined slightly relative to portion 16 in an outward sense relative to the included angle between these two portions and portion 14.

The plates 12 are of longitudinally curved, rectangular form and their opposed end edges are respectively connected with the corresponding portions 14 16 and 17 of the two members 11 to interconnect these members in a mutually transversely-spaced parallel disposition.

Each strap 13 is connected to a respective one of the plates to extend from one end thereof and is releasably connectable with the other end portion of its plate.

In an initial embodiment of this splint subjected to a clinical trial the members 11 were of metal wire such that the spiral portions 15 served as springs while the remaining portions were relatively stiff, the plates were of sheet metal to be stiff but had their concave surfaces covered with a cushioning layer of foamed plastics material 18, and the straps 13 were of textile fabric of releasably self-adhesive form.

FIG. 2 shows the usage of this splint in application to a finger 20 with the three plates respectively located dorsally over and strapped to the three phalanges, with the members 11 located along opposite sides of the finger, with the spiral portions 15 located adjacent the PIP joint 21, and with the junctions of the portions 16 and 17 located in the region of the DIP joint 22. It will be seen that this overall location is such that the DIP joint is held in slight hyperextension by virtue of the inclination between portions 16 and 17, and that the PIP joint is held in flexion by virtue of the general perpendicularity between these last portions and portions 14. Also, it will be appreciated that the PIP joint is open to limited restrained extension movement by rotation of, and against the inherent spring action of, the spiral portions 15 which bias the splint, and the finger therewith, to the configuration described above.

The splint of FIG. 1 is, of course, but one example of a practicable form of the invention and various other such forms are possible. Indeed another form is at present preferred following continued development and trial.

FIG. 3 shows this preferred form which is modified relative to that of FIG. 1 by integration of the two plates bordering the DIP joint into a one-piece plate 23. This plate 23 is generally rectangular but transversely curved to form a channel extending along and over the two distal phalanges, and having slight longitudinal angling, suitably of about 20°, part way therealong to locate the DIP joint in slight hyperextension.

Another modification is seen in that the spiral portion springs are preferably wound to close during extension of the PIP joint rather than open. This change better preserves the spring action for a given wire material.

Also, it is found unnecessary in practice to provide a strap for the proximal plate 12 because the spring force will suitably locate this plate.

It will also be noted that the plates 12 and 23 are rounded at their mutually remote ends.

The angle between the portions 14 and 16 is preferably a little less than 90° when the splint is in an unstressed state, off the finger, this angle suitably being 80° to 85°.

The overall proportions and dimensions of the splint are preferably such that, in use, the distal and proximal straps 13 are respectively located close to the end of the finger and the PIP joint, and the plate 12 is located towards the proximal end of the associated phalanx and may be slightly longitudinally upwardly inclined to seat against the adjacent knuckle. At the same time, the spiral springs preferably have their centres located in the region of the PIP joint axis.

The preferred locations just discussed can be reasonably well attained by the provision of a very modest range of sizes of splint to suit different fingers.

FIG. 4 shows another modification relative to FIG. 1 in which the middle plate, differentiated by reference numeral 24, is disposed to adopt a palmar location relative to the finger.

Clearly yet other variations are possible. For example, the proximal plate could also adopt a palmar location, but it is preferred that such a location be avoided for the distal plate so that the tactile facility is retained. The members 11 can be integrated by formation from one piece of material, with this piece extending across the proximal and/or distal plate to reinforce the same. The splint need not involve hingeing and spring action from a common structure, although this can clearly be simple and convenient in manufacture. Lastly, the supportive hinge and spring functions of the plates and members may, within the limit in terms of simplicity of structure, be served by a one-piece moulding of plastics material.

We claim:

1. An orthopaedic splint for the finger comprising a first portion and a second portion respectively for location distally and proximally of the proximal interphalangeal joint; said first portion including two plates each curved to seat in one of palmar and dorsal dispositions round a phalanx, said plates each having a respective strap to hold the same releasably so seated, and said plates being interconnected in mutually inclined manner for respective location distally and proximally of the distal interphalangeal joint to hold this joint in hyperextension; and said first and second portions being resiliently and hingedly interconnected to hold the proximal interphalangeal joint in flexion while allowing restrained extension against the spring force of this last interconnection.

2. An orthopaedic splint for the finger comprising a first portion and a second portion respectively for location distally and proximally of the proximal interphalangeal joint; said first portion including a single plate curved to seat in one of palmar and dorsal dispositions round a phalanx, said plate being elongated transversely of its curve, having a longitudinal inclination between its ends, and having individual straps at its ends for respective location distally and proximally of the distal interphalangeal joint to hold the same releasably in hyperextension; and said first and second portions being resiliently and hingedly connected to hold the proximal interphalangeal joint in flexion while allowing restrained extension against the spring force of such interconnection.

3. An orthopaedic splint for a finger comprising a first portion and a second portion respectively for location distally and proximally of the proximal interphalangeal joint, each said portion including at least one plate curved to seat in one of palmar and dorsal dispositions round a phalanx, at least said first portion plate having strapping to hold the same releasably so seated, and said first portion plating turning through an angle of about 20° longitudinally of said phalanx to hold the distal interphalangeal joint in hyperextension.

4. An orthopaedic splint for a finger comprising a first portion and a second portion respectively for location distally and proximally of the proximal interphalangeal joint, said first portion holding the distal interphalangeal joint in hyperextension, said first and second portions being resiliently and hingedly interconnected by a common spring structure to hold the proximal interphalangeal joint in flexion while allowing restrained extension against the spring force of said structure, and said structure holding said portions at a generally mutually perpendicular inclination when unstressed.

5. A splint according to claim 4 wherein said spring structure includes two like springs for location on respectively opposite sides of the PIP joint.

6. A joint according to claim 5 wherein said two springs are of mutually parallel flat spiral forms.

7. A joint according to claim 6 wherein said springs are spirally wound to close with extension of the PIP joint.

8. A method of treating injury to the extensor tendon distal to the proximal interphalangeal joint in the finger, which method comprises splinting the finger to hold the distal interphalangeal joint in hyperextension and the proximal interphalangeal joint in flexion at approximately 90°, while allowing restraint extension of the proximal interphalangeal joint.

9. A method according to claim 8 wherein the PIP joint extension is resiliently restrained.

* * * * *